(12) United States Patent
Zhang et al.

(10) Patent No.: US 9,896,576 B2
(45) Date of Patent: Feb. 20, 2018

(54) MEDICAL TUBE

(71) Applicant: Celanese EVA Performance Polymers Corporation, Irving, TX (US)

(72) Inventors: Bin Zhang, Union, KY (US); Jeffrey C. Haley, Norwood, OH (US); Dirk Hair, Edmonton (CA); Jose Reyes, Irving, TX (US); Sung Hye Kim, Erlanger, KY (US)

(73) Assignee: Celanese EVA Performance Polymers Corporation, Irving, TX (US)

( * ) Notice: Subject to any disclaimer, the term of this patent is extended or adjusted under 35 U.S.C. 154(b) by 0 days.

(21) Appl. No.: 15/334,374

(22) Filed: Oct. 26, 2016

(65) Prior Publication Data

US 2017/0121513 A1     May 4, 2017

Related U.S. Application Data

(60) Provisional application No. 62/247,845, filed on Oct. 29, 2015, provisional application No. 62/367,693, filed on Jul. 28, 2016, provisional application No. 62/396,283, filed on Sep. 19, 2016.

(51) Int. Cl.
*C08L 23/08* (2006.01)
*A61M 25/00* (2006.01)

(52) U.S. Cl.
CPC ..... *C08L 23/0853* (2013.01); *A61M 25/0021* (2013.01); *C08L 2203/02* (2013.01); *C08L 2205/025* (2013.01)

(58) Field of Classification Search
CPC ........... C08L 23/0853; C08L 2205/025; C08L 2203/02; A61M 25/0021
See application file for complete search history.

(56) References Cited

U.S. PATENT DOCUMENTS

| | | | |
|---|---|---|---|
| 2,425,389 A | 8/1947 | Oxley et al. | |
| 2,859,241 A | 11/1958 | Schnizer | |
| 3,821,333 A | 6/1974 | Goodwin et al. | |
| 3,865,776 A | 2/1975 | Gergen | |
| 3,941,859 A | 3/1976 | Batiuk et al. | |
| 4,131,654 A | 12/1978 | Herman et al. | |
| 4,243,576 A | 1/1981 | Fischer et al. | |
| 4,247,584 A | 1/1981 | Widiger et al. | |
| 4,266,542 A | 5/1981 | Becker et al. | |
| 4,309,332 A | 1/1982 | Fischer et al. | |

(Continued)

FOREIGN PATENT DOCUMENTS

WO    WO 2015/116958 A1    8/2015

OTHER PUBLICATIONS

Product Information—PFA Tubing from Parker Legris Connectic, 2011, 4 pages.

(Continued)

*Primary Examiner* — Michael C Miggins
(74) *Attorney, Agent, or Firm* — Dority & Manning, P.A.

(57) ABSTRACT

A medical tube that contains a polymer composition that is generally flexible and biocompatible is provided. The polymer composition contains at least one ethylene vinyl acetate polymer and at least one viscoelastic additive. By selectively controlling specific aspects of the ethylene vinyl acetate polymer (e.g., vinyl acetate content, melt flow index, density, etc.), the viscoelastic additive, and the manner in which they are blended, the resulting composition can exhibit a reduced tendency to kink when formed into the medical tube.

20 Claims, 3 Drawing Sheets

(56) References Cited

U.S. PATENT DOCUMENTS

| | | | |
|---|---|---|---|
| 4,707,389 A | 11/1987 | Ward | |
| 4,843,170 A | 6/1989 | Isshiki et al. | |
| 4,877,827 A | 10/1989 | Van Der Groep | |
| 5,003,178 A | 3/1991 | Livesay | |
| 5,116,652 A | 5/1992 | Alzner | |
| 5,218,036 A | 6/1993 | Kagawa et al. | |
| 5,274,035 A | 12/1993 | Chundury | |
| 5,356,709 A | 10/1994 | Woo et al. | |
| 5,399,401 A | 3/1995 | Powell | |
| 5,889,120 A | 3/1999 | O'Donnell | |
| 5,962,995 A | 10/1999 | Avnery | |
| 6,406,767 B1 | 6/2002 | Mueller | |
| 6,407,492 B1 | 6/2002 | Avnery et al. | |
| 6,569,538 B1 | 5/2003 | Kaschel | |
| 6,846,535 B2 | 1/2005 | De Groot et al. | |
| 8,956,706 B2 | 2/2015 | Siddhamalli et al. | |
| 9,133,332 B2 | 9/2015 | Kawamoto et al. | |
| 9,422,428 B2 | 8/2016 | Kaushik et al. | |
| 2008/0161438 A1 | 7/2008 | Wang et al. | |
| 2010/0222510 A1 | 9/2010 | Kelbech et al. | |
| 2011/0308731 A1 | 12/2011 | Dalmis et al. | |
| 2014/0079898 A1 | 3/2014 | Kaushik et al. | |
| 2015/0141567 A1 | 5/2015 | Hoej et al. | |
| 2015/0218365 A1 | 8/2015 | Zhang et al. | |

OTHER PUBLICATIONS

Product Information—Wear Resistant Tubing, Series TUZ, from SMC Corporation, 2008, 7 pages.

Paper—PST 522E—Synthesis and Characterization of Macromolecules, Chapter 4, "*Dynamic Mechanical Analysis of Epoxy-Carbon Fiber Composites*," pp. 25-39.

Product Data Sheet for DuPont™ Elvax® 360 from E.I. du Pont de Nemours and Company, Inc. Aug. 8, 2010, 2 pages.

Technical information on Nordel® IP 2720P from DuPont Dow Elastomers, Jun. 2002, 2 pages.

Data Sheet on Ateva® 2810A Ethylene Vinyl Acetate Copolymer from Celanese EVA Performance Polymers, 2014, 1 page.

International Search Report and Written Opinion for PCT/US2016/058814, dated Jan. 17, 2017, 9 pages.

MEDICAL TUBE

RELATED APPLICATIONS

The present application claims priority to U.S. Provisional Application Ser. Nos. 62/247,845, filed on Oct. 29, 2015, 62/367,693, filed on Jul. 28, 2016, and 62/396,283, filed on Sep. 19, 2016, which are incorporated herein in their entirety by reference thereto.

BACKGROUND OF THE INVENTION

Due to its inherent flexibility and transparency, one of the most commonly used materials to form medical tubes is polyvinyl chloride ("PVC"). A significant problem with polyvinyl chloride, however, is that it has a very high chlorine content (e.g., about 57 wt. %), which is an environmental concern and can create issues when disposing of the medical device. While different types of materials have been tried as a substitute, none are fully satisfactory. For example, many conventional elastomeric materials (e.g., vulcanized rubbers) possess a high degree of flexibility that allows them to be employed in medical tubes, but they are not typically transparent or even biocompatible. Attempts have been made to use elastomeric materials (e.g., vinyl acetate rubbers) that are relatively transparent and biocompatible, however, these materials suffer from an additional problem in that they tend to "kink" during use. As such, a need continues to exist for an improved material for use in medical tubes.

SUMMARY OF THE INVENTION

In accordance with one embodiment of the present invention, a medical tube is disclosed that comprises a wall that extends in a longitudinal direction and defines a hollow passageway. The wall comprises a polymer composition, which in turn comprises at least one ethylene vinyl acetate polymer having a vinyl acetate content of from about 15 wt. % to about 55 wt. % and at least one viscoelastic additive. The ethylene vinyl acetate polymer constitutes from about 40 wt. % to about 98 wt. % of the composition. In certain embodiments, the polymer composition may have a chlorine content of about 5,000 ppm or less.

In accordance with another embodiment of the present invention, a polymer composition for use in a medical tube is disclosed. The polymer composition comprises from about 40 wt. % to about 98 wt. % of an ethylene vinyl acetate polymer having a vinyl acetate content of from about 15 wt. % to about 45 wt. %, and from about 2 wt. % to about 60 wt. % of an ethylene vinyl acetate rubber having a vinyl acetate content from about 45 wt. % to about 90 wt. %. The ratio of the melt flow index of the ethylene vinyl acetate polymer to the melt flow index of the ethylene vinyl acetate rubber is from about 0.1 to about 30.

Other features and aspects of the present invention are set forth in greater detail below.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which:

FIGS. 3-5 illustrate a test for measuring the kink length of a sample in which FIG. 3 shows the sample in its initial bent state, FIG. 4 shows the test sample after further bending, and FIG. 5 shows the sample when a kink is formed at the location of the bend.

DETAILED DESCRIPTION

Figure 1:
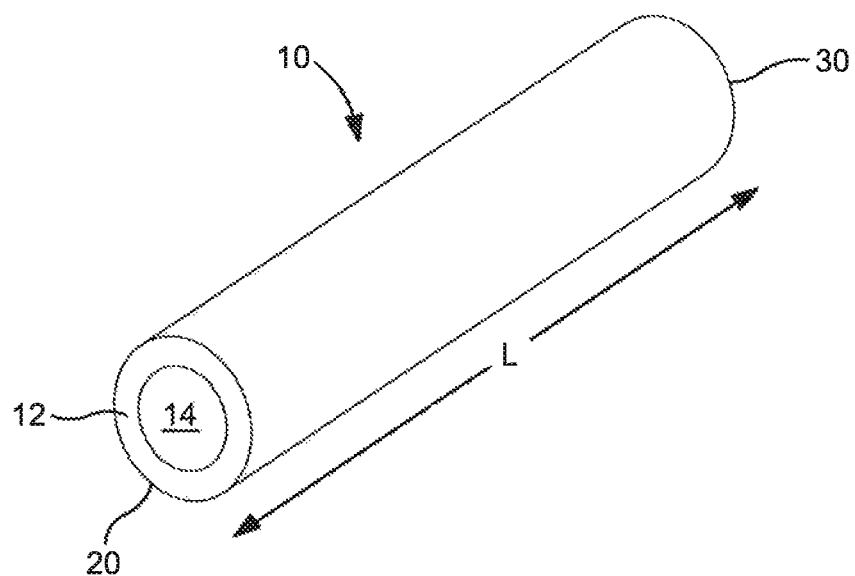
FIG. 1 is a perspective view of one embodiment of a medical tube that may be employed in the present invention.

It is to be understood by one of ordinary skill in the art that the present discussion is a description of exemplary embodiments only, and is not intended as limiting the broader aspects of the present invention.

Generally speaking, the present invention is directed to a medical tube that contains a polymer composition that is generally flexible and biocompatible. In this regard, the polymer composition contains at least one ethylene vinyl acetate polymer and at least one viscoelastic additive (e.g., elastomeric polymer or plasticizer). By selectively controlling specific aspects of the ethylene vinyl acetate polymer (e.g., vinyl acetate content, melt flow index, density, etc.), the viscoelastic additive, and the manner in which they are blended together, the present inventors have discovered that the resulting composition can exhibit a reduced tendency to kink when employed in the medical tube. The degree of kink resistance can be quantified by the "kink length", which may be about 60 millimeters or less, in some embodiments about 55 millimeters or less, and in some embodiments, from about 5 to about 50 millimeters, such as determined for a tube having an outer diameter of about 6.4 mm and wall thickness of about 0.8 mm in accordance with the test method described below. This may be normalized based on the tube diameter and thickness as described herein so that the resulting "kink length value" is about 110 or less, in some embodiments about 100 or less, and in some embodiments, from about 80 to about 95. In addition to possessing a reduced tendency to kink, the present inventors have also discovered that medical tubes formed from the polymer composition may also have other beneficial properties. The composition and resulting medical tube may, for instance, have a minimal degree of tackiness. For example, a surface of the medical tube may have a relatively low average coefficient of friction, such as about 0.300 or less, in some embodiments about 0.200 or less, and in some embodiments, from about 0.001 to about 0.150, as determined substantially in accordance with ASTM D1894-14 as described below. The composition and resulting tube are also typically transparent, which can be quantified by a "haze" value, which is a measurement of the wide angle scattering of light within the material. Namely, haze is defined as the percentage of transmitted light that deviates from the incident beam by more than an average of 25° and may be determined in accordance with ASTM D1003-13 as described below. For example, the haze of the medical tube may be 15% or less, in some embodiments about 10% or less, and in some embodiments, from about 0.1% to about 8%. Of course, an additional benefit of the polymer composition of the present invention is that it generally has a low chlorine content, such as about 5,000 ppm or less, in some embodiments about 3,000 ppm or less, in some embodiments from 0 to about 2,000 ppm, and in some embodiments, from about 1 to about 1,000 ppm.

Various embodiments of the present invention will now be described in further detail.

I. Polymer Composition

As noted above, the polymer composition contains at least one ethylene vinyl acetate polymer. Typically, such polymers constitute from about 40 wt. % to about 98 wt. %, in some embodiments from about 50 wt. % to about 95 wt. %, and in some embodiments, from about 60 wt. % to about 90 wt. % of the polymer composition. The weight ratio of the viscoelastic additive(s) to the ethylene vinyl acetate polymer(s) may likewise range from about 0.05 to about 10, in some embodiments from about 0.1 to about 5, and in some embodiments from about 0.5 to about 5. For example, viscoelastic additive(s) typically constitute from about 2 wt. % to about 60 wt. %, in some embodiments from about 5 wt. % to about 50 wt. %, and in some embodiments, from about 10 wt. % to about 50 wt. % of the polymer composition. Regardless of the relative concentration of each component, the melt flow index of the resulting composition typically ranges range from about 0.5 to about 50 grams per 10 minutes ("g/10 min"), in some embodiments from about 1 to about 40 g/10 min, and in some embodiments, from about 5 to about 30 g/10 min, as determined in accordance with ASTM D1238-13 at a temperature of 190° C. and a load of 2.16 kilograms. The melting point may also range from about 40° C. to about 100° C., in some embodiments from about 45° C. to about 95° C., and in some embodiments, from about 50° C. to about 85° C., as determined in accordance with ASTM D3418-12e1.

A. Ethylene Vinyl Acetate Polymer

As used herein, an ethylene vinyl acetate polymer is defined as a copolymer that contains at least one ethylene monomer and at least one vinyl acetate monomer. The present inventors have discovered that certain aspects of the ethylene vinyl acetate polymer can be selectively controlled to help achieve the desired properties (e.g., kink resistance). For instance, the ethylene vinyl acetate polymer is selectively controlled so that it has a vinyl acetate content of from about 15 wt. % to about 45 wt. %, in some embodiments about 20 wt. % to about 40 wt. %, and in some embodiments, from about 26 wt. % to about 38 wt. %. Within such a carefully controlled range, the present inventors have found that the resulting composition can exhibit good kink resistance and transparency, but also have a minimal degree of tackiness.

The density of the ethylene vinyl acetate polymer may also range from about 0.900 to about 1.00 grams per cubic centimeter (g/cm$^3$), in some embodiments from about 0.910 to about 0.980 g/cm$^3$, and in some embodiments, from about 0.930 to about 0.960 g/cm$^3$, as determined in accordance with ASTM D792-13. Still further, the melt flow index of the ethylene vinyl acetate polymer may range from about 0.5 to about 100 g/10 min, in some embodiments from about 5 to about 80 g/10 min, and in some embodiments, from about 10 to about 70 g/10 min, as determined in accordance with ASTM D1238-13 at a temperature of 190° C. and a load of 2.16 kilograms. The melting point may also range from about 30° C. to about 100° C., and in some embodiments, from about 40° C. to about 85° C., as determined in accordance with ASTM D3418-12e1. Examples of suitable ethylene vinyl acetate polymers that may be employed include those available from Celanese under the designation ATEVA® (e.g., ATEVA® 2810 or 4030C); DuPont under the designation ELVAX® (e.g., ELVAX® 260 or 40W); and Arkema under the designation EVATANE® (e.g., EVATANE 28-05).

Any of a variety of techniques may generally be used to form the ethylene vinyl acetate polymer with the desired properties as is known in the art. In one embodiment, the polymer is produced by copolymerizing an ethylene monomer and a vinyl acetate monomer in a high pressure reaction. Vinyl acetate may be produced from the oxidation of butane to yield acetic anhydride and acetaldehyde, which can react together to form ethylidene diacetate. Ethylidene diacetate can then be thermally decomposed in the presence of an acid catalyst to form the vinyl acetate monomer. Examples of suitable acid catalysts include aromatic sulfonic acids (e.g., benzene sulfonic acid, toluene sulfonic acid, ethylbenzene sulfonic acid, xylene sulfonic acid, and naphthalene sulfonic acid), sulfuric acid, and alkanesulfonic acids, such as described in U.S. Pat. No. 2,425,389 to Oxley et al.; U.S. Pat. No. 2,859,241 to Schnizer; and U.S. Pat. No. 4,843,170 to Isshiki et al. The vinyl acetate monomer can also be produced by reacting acetic anhydride with hydrogen in the presence of a catalyst instead of acetaldehyde. This process converts vinyl acetate directly from acetic anhydride and hydrogen without the need to produce ethylidene diacetate. In yet another embodiment, the vinyl acetate monomer can be produced from the reaction of acetaldehyde and a ketene in the presence of a suitable solid catalyst, such as a perfluorosulfonic acid resin or zeolite.

B. Viscoelastic Additive

As indicated above, the polymer composition of the present invention also contains a viscoelastic additive that has the effect of modifying the viscoelasticity of the ethylene vinyl acetate polymer so that the resulting composition is relatively resistant to kinking. In certain embodiments, for example, a flexible polymeric material (e.g., olefinic polymer) may be employed that can increase the elastic modulus of the composition, thereby enhancing the degree of kink resistance. The flexible polymeric material is typically selected to have a relatively low melt flow index (or high viscosity) in comparison to the ethylene vinyl acetate polymer to ensure that the materials can be adequately blended together without having an adverse impact on the mechanical properties of the resulting composition. For example, the ratio of the melt flow index of the ethylene vinyl acetate polymer to the melt flow index of the flexible polymeric material, when employed, is typically from about 0.1 to about 30, in some embodiments from about 1 to about 30, in some embodiments from about 2 to about 25, and in some embodiments, from about 5 to about 20. The flexible polymeric material may, for example, have a melt flow index of from about 0.1 to about 30 grams per 10 minutes, in some embodiments from about 0.2 to about 20 grams per 10 minutes, and in some embodiments, from about 0.5 to about 5 grams per 10 minutes, determined at a load of 2.16 kilograms and at 190° C. in accordance with ASTM D1238-13.

While a wide variety of polymers may be employed that have the properties identified above, olefinic polymers are particularly suitable for use in the present invention. Such olefinic polymers may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, olefin-diene copolymers, vinyl acetate rubbers, polyvinyl acetate, and so forth.

In one embodiment, the olefinic polymer may include a copolymer of propylene with one or more additional monomers (e.g., α-olefin, diene, etc.). A specific example of such a copolymer ethylene-propylene-diene ("EPDM"), such as available from Dow Chemical under the trade designation NORDEL® IP. In yet another embodiment, the olefinic polymer may include a copolymer of propylene with an α-olefin monomer, such as a $C_2$-$C_{20}$ α-olefin. Specific examples of suitable α-olefins include ethylene, 1-butene, 3-methyl-1-butene, 3,3-dimethyl-1-butene, 1-pentene, 1-pentene with one or more methyl, ethyl or propyl substituents, 1-hexene with one or more methyl, ethyl or propyl substituents, 1-heptene with one or more methyl, ethyl or propyl substituents, 1-octene with one or more methyl, ethyl or propyl substituents, 1-nonene with one or more methyl, ethyl or propyl substituents, ethyl, methyl or dimethyl-substituted 1-decene, 1-dodecene, and styrene. A suitable α-olefin comonomer is ethylene. The propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

One particularly suitable example of an olefinic polymer is an ethylene vinyl acetate rubber having a relatively high vinyl acetate content. For instance, the ethylene vinyl acetate rubber may have a vinyl acetate content of from about 45 wt. % to about 95 wt. %, in some embodiments about 46 wt. % to about 90 wt. %, and in some embodiments, from about 48 wt. % to about 85 wt. %. A specific example of such an ethylene vinyl acetate rubber is available from Lanxess under the trade designation LEVAPREN® 800 (80 wt. % vinyl acetate), LEVAMELT® 800 (80 wt. % vinyl acetate), or LEVAMELT® 500 (50 wt. % vinyl acetate). In such embodiments, the ratio of the melt flow index of the ethylene vinyl acetate polymer to the melt flow index of the ethylene vinyl acetate rubber is typically from about 0.1 to about 30, in some embodiments from 5 to about 30, in some embodiments from about 10 to about 25, and in some embodiments, from about 12 to about 20. Likewise, in such embodiments, the ethylene vinyl acetate rubber typically has a melt flow index of from about 0.1 to about 10 grams per 10 minutes, in some embodiments from about 0.2 to about 8 grams per 10 minutes, and in some embodiments, from about 0.5 to about 5 grams per 10 minutes, determined at a load of 2.16 kilograms and at 190° C. in accordance with ASTM D1238-13.

C. Optional Additives

To maintain the desired properties, a substantial portion of the composition is generally formed from ethylene vinyl acetate polymers and viscoelastic additives. That is, about 50 wt. % or more, in some embodiments from about 60 wt. % to about 99 wt. %, and in some embodiments, from about 70 wt. % to about 95 wt. % of the composition is formed by such components. Nevertheless, the composition may optionally contain one or more additives if so desired, such as plasticizers, flow aids, antimicrobials, fillers pigments, antioxidants (e.g., hindered phenols), stabilizers, surfactants, waxes, solid solvents, flame retardants, anti-drip additives, crosslinking agents, pro-radical additives, and other materials added to enhance properties and processability. When employed, the optional additive(s) typically constitute from about 0.1 wt. % to about 50 wt. %, and in some embodiments, from about 1 wt. % to about 40 wt. %, and in some embodiments, from about 5 wt. % to about 30 wt. % of the composition.

In certain embodiments, for example, a plasticizer may be employed that can further enhance the overall flexibility of the polymer composition. A variety of suitable plasticizers may be employed in the present invention for this purpose. In one embodiment, for instance, the plasticizer may include an ester of a fatty acid, such as phthalic acid, isophthalic acid, adipic acid, azelaic acid, sebacic acid, maleic acid, fumaric acid, trimellitic acid, oleic acid, citric acid, itaconic acid, stearic acid, etc., as well as combinations thereof. Particular examples of such esters include dimethyl phthalate, diethyl phthalate, dibutyl phthalate, di-(2-ethylhexyl) phthalate, di-n-octyl phthalate, diisobutyl phthalate, diheptyl phthalate, diphenyl phthalate, diisodecyl phthalate, ditridecyl phthalate, diundecyl phthalate, di(heptyl, nonyl, undecyl) phthalate, benzyl phthalate, butylbenzyl phthalate, dinonyl phthalate, dicyclohexyl phthalate, dimethyl isophthalate, di-(2-ethylhexyl) isophthalate, and diisooctyl disophthalate, di-n-butyl adipate, di-(2-ethylhexyl) adipate, diisodecyl adipate, diisononyl adipate, di-(2-ethylhexyl) azelate, diisooctyl azelate, and di-n-hexyl azelate; di-n-butyl sebacate, di-(2-ethylhexyl) sebacate, diisodecyl sebacate, di-n-butyl maleate, dimethyl maleate, diethyl maleate, di-(2-ethylhexyl) maleate, di-n-butyl fumarate, di-(2-ethylhexyl) fumarate, tri(2-ethyl-hexyl) trimellitate, tri-n-octyl trimellitate, triisodecyl trimellitate, triisooctyl trimellitate, tri-n-hexyl trimellitate, and triisononyl trimellitate, triethyl citrate, tri-n-butyl citrate, acetyl triethyl citrate, acetyl tri-(2-ethylhexyl) citrate, monomethyl itacontate, monobutyl itacontate, dimethyl itaconate, diethyl itaconate, dibutyl itaconate, di(2-ethylhexyl) itaconate, butyl oleate, glyceryl monooleate, diethylene glycol monooleate, n-butyl stearate, glycerin monostearate, diethylene glycol distearate, and so forth.

Other suitable plasticizers may include phosphoric acid derivatives, such as triethyl phosphate, tributyl phosphate, tri-(2-ethylhexyl) phosphate, tributoxyethyl phosphate, triphenyl phosphate, cresyl dipenyl phosphate, tricresyl phosphate, trixylenyl phosphate, and tris(chloroethyl) phosphate; glycol derivatives, such as diethylene glycol dibenzoate, dipropylene glycol dibenzoate, triethylene glycol di-(2-ethylbutyrate), triethylene glycol di-(2-ethylhexoate), dibutyl-methylenebisthio-glycolate; glycerin derivatives, such as glycerol monoaceate, glycerol triacetate, and glycerol tributyrate; epoxy derivatives such as epoxylated soy bean oil, epoxybutyl stearate, 2-ethylhexyl epoxyhexahydrophthalate, diisodecyl epoxyhexahydrophthalate, epoxytriglyceride, epoxylated octyl oleate, and epoxylated decyl oleate; polyesters; polyethers; and so forth.

II. Melt Blending

Generally speaking, the ethylene vinyl acetate polymer, viscoelastic additive, and other optional additives may be melt blended together to form the polymer composition. Melt blending may occur at a temperature range of from about 60° C. to about 260° C., in some embodiments, from about 80° C. to about 250° C., and in some embodiments, from about 100° C. to about 220° C. to form the polymer composition.

Any of a variety of melt blending techniques may generally be employed in the present invention. For example, the components may be supplied separately or in combination to an extruder that includes at least one screw rotatably mounted and received within a barrel (e.g., cylindrical barrel). The extruder may be a single screw or twin screw extruder. For example, one embodiment of a single screw extruder may contain a housing or barrel and a screw rotatably driven on one end by a suitable drive (typically including a motor and gearbox). If desired, a twin-screw extruder may be employed that contains two separate screws. The configuration of the screw is not particularly critical to the present invention and it may contain any number and/or orientation of threads and channels as is known in the art. For example, the screw typically contains a thread that forms a generally helical channel radially extending around a core of the screw. A feed section and melt section may be defined along the length of the screw. The feed section is the input portion of the barrel where the ethylene vinyl acetate polymer and/or viscoelastic additive are added. The melt section is the phase change section in which the polymer is changed from a solid to a liquid. While there is no precisely defined delineation of these sections when the extruder is manufactured, it is well within the ordinary skill of those in this art to reliably identify the feed section and the melt section in which phase change from solid to liquid is occurring. Although not necessarily required, the extruder may also have a mixing section that is located adjacent to the output end of the barrel and downstream from the melting section. If desired, one or more distributive and/or dispersive mixing elements may be employed within the mixing and/or melting sections of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin mixers.

If desired, the ratio of the length ("L") to diameter ("D") of the screw may be selected to achieve an optimum balance between throughput and blending of the components. The L/D value may, for instance, range from about 15 to about 50, in some embodiments from about 20 to about 45, and in some embodiments from about 25 to about 40. The length of the screw may, for instance, range from about 0.1 to about 5 meters, in some embodiments from about 0.4 to about 4 meters, and in some embodiments, from about 0.5 to about 2 meters. The diameter of the screw may likewise be from about 5 to about 150 millimeters, in some embodiments from about 10 to about 120 millimeters, and in some embodiments, from about 20 to about 80 millimeters. In addition to the length and diameter, other aspects of the extruder may also be selected to help achieve the desired degree of blending. For example, the speed of the screw may be selected to achieve the desired residence time, shear rate, melt processing temperature, etc. For example, the screw speed may range from about 50 to about 800 revolutions per minute ("rpm"), in some embodiments from about 70 to about 500 rpm, and in some embodiments, from about 80 to about 400 rpm. The apparent shear rate during melt blending may also range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

III. Crosslinking

Although by no means required, the polymer composition of the present invention can optionally be "crosslinked" to the extent that at least one polymer within the composition is bonded to itself or another polymer. For example, the ethylene vinyl acetate polymer, viscoelastic additive, or both may be crosslinked prior to being melt blended together. Likewise, crosslinking may also occur after melt blending the ethylene vinyl acetate polymer and viscoelastic additive, either before or after forming a medical device from the blended polymer composition. Crosslinking is typically achieved through the formation of free radicals (unpaired electrons) that link together to form a plurality of carbon-carbon covalent bonds at the monomer units of one or more polymers (e.g., ethylene vinyl acetate polymer and/or viscoelastic additive). Such free radical formation may be induced through a wide variety of known techniques, such as through chemical crosslinking (e.g., in the presence of a crosslinking agent), electromagnetic radiation, etc. Suitable crosslinking agents may include, for instance, organic peroxide compounds, such as dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, etc. In one particular embodiment, the crosslinking is induced by subjecting the polymer composition to electromagnetic radiation. Some suitable examples of electromagnetic radiation that may be used include, for instance, ultraviolet light, electron beam radiation, radioisotopes (e.g., alpha particles, beta particles, gamma radiation, etc.), x-rays, neutron beams, positively-charged beams, laser beams, and so forth. Electron beam radiation, for instance, involves the production of accelerated electrons by an electron beam device, such as described in U.S. Pat. No. 5,003,178 to Livesay; U.S. Pat. No. 5,962,995 to Avnery, and U.S. Pat. No. 6,407,492 to Avnery, et al.

When supplying electromagnetic radiation, it may be desired to selectively control various parameters of the radiation to enhance the degree of crosslinking of the ethylene vinyl acetate polymer and/or viscoelastic additive. For example, one parameter that may be controlled is the wavelength of the electromagnetic radiation. For example, the wavelength may be about 1000 nanometers or less, in some embodiments about 100 nanometers or less, and in some embodiments, about 1 nanometer or less. Electron beam radiation, for instance, typically has a wavelength of about 1 nanometer or less. Besides selecting the particular wavelength, other parameters may also be selected to optimize the degree of crosslinking. For example, higher dosage and energy levels of radiation will typically result in a higher degree of crosslinking; however, it is generally desired that the composition not be "overexposed" to radiation to avoid an unwanted level of degradation. Thus, in some embodiments, the dosage may range from about 0.1 kiligrays (KGy) to about 200 KGy, in some embodiments, from about 0.5 KGy to about 150 KGy, and in some embodiments, from about 1 KGy to about 100 KGy. In addition, the energy level may also range from about 0.05 Megaelectron volts (MeV) to about 600 MeV. Of course, it should be understood that the actual dosage and/or energy level required depends on the type of polymers and electromagnetic radiation. Specifically, certain types of polymers may tend to form a lesser or greater number of crosslinks, which will influence the dosage and energy of the radiation utilized. Likewise, certain types of electromagnetic radiation may be less effective in crosslinking the polymer, and thus may be utilized at a higher dosage and/or energy level. For instance, electromagnetic radiation that has a relatively high wavelength (lower frequency) may be less efficient in crosslinking the polymer than electromagnetic radiation having a relatively low wavelength (higher frequency). Accordingly, in such instances, the desired dosage and/or energy level may be increased to achieve the desired degree of crosslinking.

IV. Medical Tube

Once formed, the polymer composition may be shaped into a tubular wall using techniques as is known in the art. For example, the polymer composition can be shaped into the desired form using an extrusion process (e.g., tubular trapped bubble film processes, flat or tube cast film processes, slit die flat cast film processes, etc.), injection molding, blow molding, overmolding, thermoforming, etc. Regardless of the manner in which it is formed, the resulting wall of the medical tube may have a variety of different configurations. In one embodiment, for instance, the wall may include only a single layer, which is formed from the polymer composition of the present invention. Alternatively, the wall may include multiple layers, one or more of which are formed from the polymer composition of the present invention. In such embodiments, the wall may contain a base layer that constitutes about 50% to 98%, in some embodiments from about 60% to about 95%, and in some embodiments, from about 70% to about 90% of the thickness of the device. If desired, the base layer may be formed from the polymer composition of the present invention. Additional layers of such multi-layered medical devices may also include, for instance, reinforcing layers, adhesive layers, barrier layers, chemically resistant layers, metal layers, etc.

Figure 2:
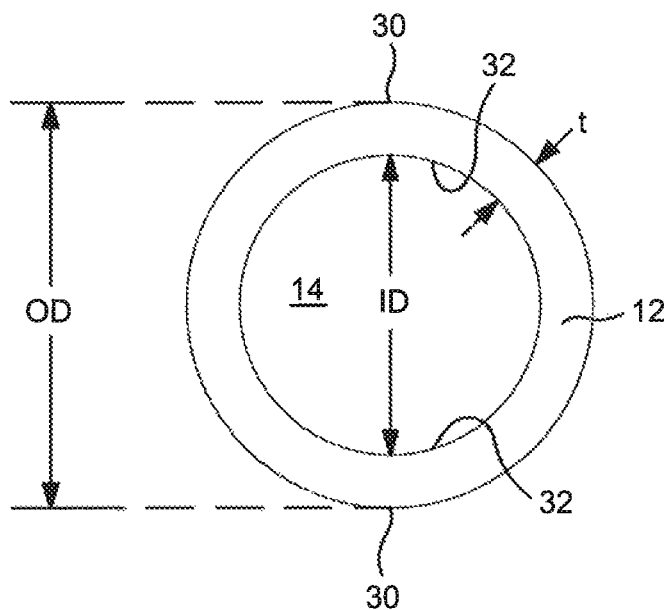
FIG. 2 is a cross-sectional view of the medical tube of FIG. 1.

Referring to FIGS. 1-2, one particular embodiment of a medical tube 10 that may be employed in the present invention is shown. As depicted, the tube 10 contains a wall 12 that extends in a longitudinal direction "L" from a first end 20 to a second end 30 and defines a hollow passageway 14 therebetween. The length of the tube 10 in the longitudinal direction may vary as desired, but is typically from about 1 to about 50 centimeters, in some embodiments from about 2 to about 40 centimeters, and in some embodiments, from about 3 to about 20 centimeters. Further, although the cross-sectional shape of the tube 10 is depicted as being circular, it should be understood other shapes may also be employed, such as ovular, rectangular, square, etc. The wall 12 also has a thickness "t" that is defined between an outer surface 30 and interior surface 32, which typically ranges from about 0.1 to about 5 millimeters, in some embodiments from about 0.2 to about 3 millimeters, and in some embodiments, from about 0.4 to about 2 millimeters. The tube 10 may also have an outer diameter ("OD") that is defined between the outer surfaces 30 of the wall 12 and an inner diameter ("ID") that is defined between the interior surfaces 32 of the wall 12. The tube may be provided with any useful diameter size suitable for the given application. In one embodiment, for instance, the tube may have an outside diameter (OD) of from about 0.1 to about 30 millimeters, in some embodiments from about 0.5 to about 20 millimeters, and in some embodiments, from about 1 to about 10 millimeters. The inside diameter (ID) of from about 0.1 to about 20 millimeters, in some embodiments from about 0.2 to about 10 millimeters, and in some embodiments, from about 0.5 to about 5 millimeters.

As noted above, the medical tube may be less resistant to kinking and also exhibit minimal tackiness. Despite exhibiting these properties, the present inventors have discovered that the tensile mechanical properties are not adversely impacted. For example, the tube may exhibit a tensile strength of from about 0.1 to about 20 MPa, in some embodiments from about 0.5 to about 15 MPa, and in some embodiments, from about 1 to about 10 MPa; a tensile break strain of about 350% or more, in some embodiments from about 400% to about 1,000%, and in some embodiments, from about 500% to about 800%; and/or a tensile modulus of from about 0.5 MPa to about 30 MPa, in some embodiments from about 1 MPa to about 25 MPa, and in some embodiments, from about 2 MPa to about 15 MPa. The tensile properties may be determined in accordance with ISO Test No. 527 (technically equivalent to ASTM D638) at 23° C.

Regardless of its particular size and shape, the resulting tube may be used to transport a variety of different types of materials during a medical procedure. For example, the medical tube may be used to convey blood, drugs, fluids and other therapies and/or materials to and from the body on a temporary or semi-permanent or permanent basis. The tube may also be used in applications such as for nutrition bags, blood bags, dialysis, urethral catheters, cardiovascular catheters, intravenous catheters, other specialty catheters, etc.

The present invention may be better understood with reference to the following examples.

Test Methods

Melt Flow Index: The melt flow index may be determined in accordance with ASTM D1238-13 at a load of 2.16 kilograms and a temperature of 190° C.

Melting and Glass Transition Temperature: The melting temperature ("Tm") and glass transition temperature ("Tg") may be determined by differential scanning calorimetry ("DSC") in accordance with ASTM D3418-12e1. Under the DSC procedure, samples may be heated and cooled at 20° C. per minute as stated in ISO Standard 10350 using DSC measurements conducted on a TA Q2000 Instrument.

Figure 3:
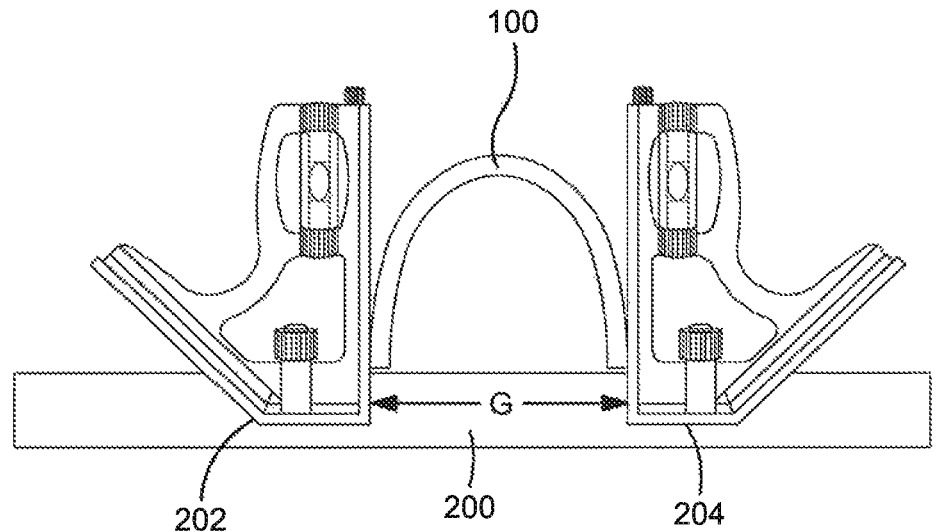
Figure 4:
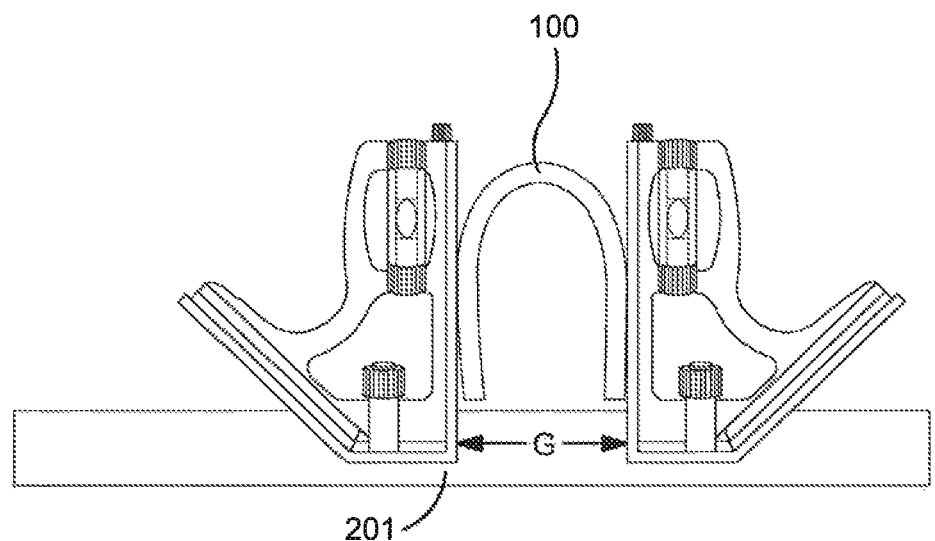
Figure 5:
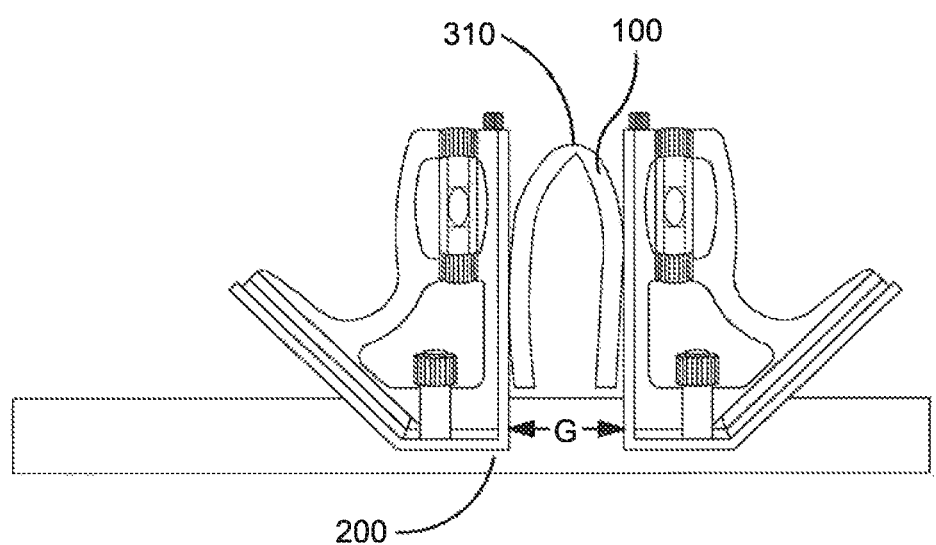

Kink Resistance: The kink resistance of a tubing sample having a target outer diameter ("OD") of 6.4 mm and wall thickness ("WT") of 0.8 mm (WT/OD=0.125) may generally be determined by measuring the "kink" length of the sample when bent. The test may be performed in the manner shown in FIGS. 3-5. More particularly, as shown in FIG. 3, the sample 100 may be initially bent by hand. A ruler 200 having a first moveable end 202 and a second fixed end 204 may then be attached to both ends of the sample so that the initial gap "G" between the ends of the sample is about 80 mm. Referring to FIGS. 4-5, the first end 202 of the ruler 200 is thereafter moved inwardly to close the gap and further bend the tubing sample 100 until a kink 300 is observed. The length of the gap "G" between the ends of the sample 100 when the kink 300 (FIG. 5) is observed is then recorded. A minimum of five (5) samples are tested and the average gap length is calculated and reported as the "kink length" value. The "kink length" is then normalized to account for any differences in the actual dimension of the tube relative to the target dimension. More particularly, a calibration line is initially generated from a single formulation in which kink length is measured for multiple WT/OD values ranging from 0.100 to 0.135. A line graph is generated with the measured king length values on the −y axis and the WT/OD values on the −x axis. The actual measured kink length and ratio of wall thickness to outer diameter is then plotted on the graph and a test line is drawn having the same slope as the calibration line. Using this test line, the kink length value is then determined for the target WT/OD ratio of 0.125. This "kink length value" may be reported as the normalized kink length for comparison between formulations.

Tackiness: The degree of tackiness may be quantified by determining the coefficient of friction of a sample. The coefficient of friction may be determined in accordance with ASTM D1894-14, with the exception that the testing sample is either a 2-inch polymer disc or an 8"×3" polymer plaque, and the load on the testing sample is 200 grams-force.

Haze: The transparency of a device may be characterized by the haze value, which can be determined in accordance with ASTM D1003-13.

Tensile Modulus, Tensile Stress, and Tensile Elongation: Tensile properties may be tested according to ISO Test No. 527 (technically equivalent to ASTM D638). Modulus and strength measurements may be made on the same test strip sample having a length of 80 mm, thickness of 10 mm, and width of 4 mm with a grip separation of 50 millimeters. The testing temperature may be 23° C. and the testing speed may be 50 mm/min.

EXAMPLE 1

A sample may be formed from a blend of 90 wt. % ethylene vinyl acetate (33% vinyl acetate content) and 10 wt. % of ethylene vinyl acetate rubber (50% vinyl acetate content). More particularly, a Coperion ZSK twin screw extruder may be used for the compounding step. The barrel diameter is 25 mm with a L/D of 40. Co-rotating intermeshing twin screws are used with single flyers in the feeding zone. In the six barrel temperature zones, the temperatures are set to 50° C., 100° C., 120° C., 120° C., 120° C. and 120° C., respectively. Vacuum may be applied at the end of the extruder with vacuum in the range of 25-30 in Hg. The temperature of the two hold die plate may be in the range of 120-140° C. The screw speed may be in the range of 200-280 rpm with a throughput in the range of 32-37 lb/hr. The melt temperature may be in the range of 160-170° C. The strand may be cooled using a 16 feet strand bath and then pelletized by a Cumberland pelletizer.

Once formed, the compounded material may be extruded into a single layer tube having a target outer diameter of about 6.4 mm, wall thickness of 0.8 mm, and a length of about 18 cm. To form the tubing, a sterling single screw extruder may be employed. The barrel diameter may be 1.5 inches with a L/D of 25. A general purpose screw may be used with a compression ratio of 3:1. Only a breaker plate may be used. In the three barrel temperature zones, the temperatures may be set to 115° C., 145° C. and 180° C., respectively. The set temperatures of the clamp ring, the die body, and the die tip may all be 190° C. The screw speed may be in the range of 17-23 rpm with a line speed in the range of 14-35 feet/min. A tubing die with a sizing ring of 10 mm outer diameter and 1 mm wall thickness may be used. The tubing dimension may be achieved by adjusting the line speed and extruder speed. A vacuum box with cooling water may also be used to control the tubing dimension and ensure the roundness. The vacuum box may be placed 70 to 150 mm away from the die tip.

The measured kink length is 45.0 mm±0.7 mm and the normalized "kink length" value is calculated as described above to be 90.

EXAMPLE 2

A sample may be formed as described in Example 1, except that the blend contains 80 wt. % ethylene vinyl acetate (40% vinyl acetate content) and 20 wt. % of ethylene vinyl acetate rubber (80% vinyl acetate content). Further, once the compounded material is formed, it is subjected to 5 kilograys (KGy) of e-beam irradiation. The crosslinked material has a melt index of 16.6 grams per 10 minutes. The crosslinked material may then be extruded into a single layer tube as described in Example 1. The measured kink length is 43.8 mm±1.8 mm and the normalized "kink length" value is calculated as described above to be 88.

The samples of Example 1 and 2 are also tested for tensile properties as described above. The results are set forth in the table below.

| | Tensile Modulus (MPa) | Tensile Break Strain (%) | Tensile Strength (MPa) |
|---|---|---|---|
| Example 1 (not crosslinked) | 9 | 670 | 5.2 |
| Example 2 (crosslinked) | 4 | 781 | 3.0 |

EXAMPLE 3

A sample may be formed as described in Example 1, except that the blend contains 80 wt. % ethylene vinyl acetate (33% vinyl acetate content) and 20 wt. % of ethylene vinyl acetate rubber (50% vinyl acetate content). The material may then be extruded into a single layer tube as described in Example 1. The measured kink length is 41.2 mm±0.8 mm and the normalized "kink length" value is calculated as described above to be 83.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A medical tube comprising a wall that extends in a longitudinal direction and defines a hollow passageway, wherein the wall comprises a polymer composition and wherein the polymer composition comprises an ethylene vinyl acetate polymer having a vinyl acetate content of from about 15 wt. % to about 45 wt. % and a viscoelastic additive, wherein the ethylene vinyl acetate polymer constitutes from about 50 wt. % to about 95 wt. % of the composition and the viscoelastic additive comprises from about 5 wt. % to about 50 wt. % of the composition, wherein the viscoelastic additive comprises an ethylene vinyl acetate rubber having a vinyl acetate content from about 45 wt. % to about 90 wt. %.

2. The medical tube of claim 1, wherein the ethylene vinyl acetate polymer has a density of from about 0.900 to about 1.00 grams per cubic centimeter.

3. The medical tube of claim 1, wherein the ethylene vinyl acetate polymer has a melt flow index of from about 0.5 to about 100 grams per 10 minutes as determined in accordance with ASTM D1238-13 at a temperature of 190° C. and a load of 2.16 kilograms.

4. The medical tube of claim 1, wherein the ethylene vinyl acetate polymer has a melting point of from about 30° C. to about 100° C.

5. The medical tube of claim 1, wherein the ratio of the melt flow index of the ethylene vinyl acetate polymer to the melt flow index of the ethylene vinyl acetate rubber is from about 0.1 to about 30.

6. The medical tube of claim 1, wherein the weight ratio of the viscoelastic additive to the ethylene vinyl acetate polymer is from about 0.05 to about 10.

7. The medical tube of claim 1, wherein the composition has a melt flow index of from about 0.5 to about 50 grams per 10 minutes as determined in accordance with ASTM D1238-13 at a temperature of 190° C. and a load of 2.16 kilograms.

8. The medical tube of claim 1, wherein the composition has a chlorine content of about 5,000 ppm or less.

9. The medical tube of claim 1, wherein the tube exhibits a kink length of about 60 millimeters or less.

10. The medical tube of claim 1, wherein the tube exhibits a normalized kink length value of about 110 or less.

11. The medical tube of claim 1, wherein the tube exhibits a haze value of about 15% or less as determined in accordance with ASTM D1003-13.

12. The medical tube of claim 1, wherein the wall contains only a single layer, the layer being formed from the polymer composition.

13. The medical tube of claim 1, wherein the wall contains multiple layers, at least one of the layers being formed from the polymer composition.

14. The medical tube of claim 1, wherein the tube has a circular cross-sectional shape.

15. The medical tube of claim 1, wherein the wall has a thickness of from about 0.1 to about 5 millimeters.

16. The medical tube of claim 1, wherein the tube has an outer diameter of from about 0.1 to about 30 millimeters.

17. The medical tube of claim 1, wherein the ethylene vinyl acetate polymer has a vinyl acetate content of from about 20 wt. % to about 40 wt. % and the ethylene vinyl acetate rubber has a vinyl acetate content from about 48 wt. % to about 85 wt. %.

18. The medical tube of claim 1, wherein the polymer composition is crosslinked.

19. The medical tube of claim 1, wherein the ethylene vinyl acetate polymer has a melt flow index of from about 0.5 to about 100 grams per 10 minutes as determined in accordance with ASTM D1238-13 at a temperature of 190° C. and a load of 2.16 kilograms.

20. The medical tube of claim 1, wherein the ethylene vinyl acetate rubber has a melt flow index of from about 0.1 to about 10 grams per 10 minutes as determined at a load of 2.16 kilograms and at 190° C. in accordance with ASTM D1238-13.

* * * * *